(12) United States Patent
Luyken et al.

(10) Patent No.: US 6,251,229 B1
(45) Date of Patent: Jun. 26, 2001

(54) PROCESS FOR THE SEPARATION OF 2-AMINOMETHYLCYCLOPENTYLAMINE FROM A MIXTURE CONTAINING HEXAMETHYLDIAMINE AND 2-AMINOMETHYLCYCLOPENTYLAMINE

(75) Inventors: Hermann Luyken, Ludwigshafen; Alwin Rehfinger, Mutterstadt; Peter Bassler, Viernheim; Guido Voit, Schriesheim; Rolf Fischer, Heidelberg; Martin Merger, Frankenthel; Harald Rust, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/254,560

(22) PCT Filed: Aug. 28, 1997

(86) PCT No.: PCT/EP97/04687

§ 371 Date: Mar. 10, 1999

§ 102(e) Date: Mar. 10, 1999

(87) PCT Pub. No.: WO98/11052

PCT Pub. Date: Mar. 19, 1998

(30) Foreign Application Priority Data

Sep. 10, 1996 (DE) .............................................. 196 36 764

Feb. 7, 1997 (DE) .............................................. 197 04 617

(51) Int. Cl.[7] .............................. B01D 3/10; C07C 209/86
(52) U.S. Cl. .......................... 203/91; 203/100; 564/437; 564/499
(58) Field of Search .................................. 203/91, 2, 100; 202/158; 564/499, 497, 437, 498, 492

(56) References Cited

U.S. PATENT DOCUMENTS

| | | | |
|---|---|---|---|
| 3,696,153 | * 10/1972 | Kershaw et al. | 502/177 |
| 3,775,258 | * 11/1973 | Kershaw | 203/29 |
| 5,133,838 | * 7/1992 | Sieja | 203/91 |
| 5,192,399 | * 3/1993 | Sieja | 203/91 |
| 5,961,788 | * 10/1999 | Ostermaier | 564/498 |

FOREIGN PATENT DOCUMENTS

| | | |
|---|---|---|
| 9636766 | * 3/1998 | (DE) . |
| 319434 | * 6/1989 | (EP) . |
| 9834903 | * 8/1998 | (WO) . |

* cited by examiner

*Primary Examiner*—Virginia Manoharan
(74) *Attorney, Agent, or Firm*—Keil & Weinkauf

(57) ABSTRACT

A process for separating 2-aminomethylcyclopentylamine from a mixture consisting of hexamethylenediamine and 2-aminomethylcyclopentylamine by distilling the mixture at a pressure from 1 to 300 mbar.

9 Claims, No Drawings

PROCESS FOR THE SEPARATION OF 2-AMINOMETHYLCYCLOPENTYLAMINE FROM A MIXTURE CONTAINING HEXAMETHYLDIAMINE AND 2-AMINOMETHYLCYCLOPENTYLAMINE

DESCRIPTION

The present invention relates to a process for separating 2-aminomethylcyclopentylamine (AMCPA) from a mixture comprising hexamethylenediamine and AMCPA.

The complete hydrogenation of adiponitrile to hexamethylenediamine and also the partial hydrogenation with coproduction of hexamethylenediamine and 6-aminocapronitrile in the presence of a catalyst based on a metal such as nickel, cobalt, iron, rhodium or ruthenium are generally known, for example from: K. Weissermel, H.-J. Arpe, Industrielle Organische Chemie, 3rd edition, VCH Verlagsgesellschaft mbH, Weinheim, 1988, page 266, U.S. Pat. No. 4,601,859, U.S. Pat. No. 2,762,835, U.S. Pat. No. 2,208,598, DE-A 848 654, DE-A 954 416, DE-A 42 35 466, U.S. Pat. No. 3,696,153, DE-A 19500222, WO 92/21650 and German Application 19548289.1.

Byproducts include hexamethyleneimine (HMI), 1,2-diaminocyclohexane (DACH) and AMCPA.

U.S. Pat. No. 3,696,153 discloses that the hexamethylenediamine obtained by this hydrogenation comprises AMCPA as a byproduct which is very difficult to separate from the mixture.

It is an object of the present invention to provide a process for separating AMCPA from a mixture comprising essentially hexamethylenediamine and AMCPA in a technically simple and economical manner.

We have found that this object is achieved by a process for separating 2-aminomethylcyclopentylamine from a mixture comprising hexamethylenediamine and 2-aminomethylcyclopentylamine, which comprises performing the separation by distilling at a pressure from 1 to 200 mbar.

The partial or complete hydrogenation of adiponitrile can be carried out according to any of the known processes, for example according to one of the aforementioned processes described in U.S. Pat. No. 4,601,859, U.S. Pat. No. 2,762,835, U.S. Pat. No. 2,208,598, DE-A 848 654, DE-A 954 416, DE-A 4 235 466, U.S. Pat. No. 3,696,153, DE-A 9 500 222 or WO 92/21650 by, in general, performing the hydrogenation in the presence of nickel-, cobalt-, iron- or ruthenium-containing catalysts. The catalysts used can be supported or unsupported catalysts. Possible supports include, for example, aluminum oxide, silicon dioxide, titanium dioxide, magnesium oxide, activated carbons and spinels. Examples of unsupported catalysts are Raney nickel and Raney cobalt.

The hydrogenation gives rise to a mixture comprising hexamethylenediamine and AMCPA with or without 6-aminocapronitrile and adiponitrile.

The separation from a mixture comprising hexamethylenediamine and AMCPA can be effected in a conventional manner, preferably by distillation, for example as described in DE-A 195 002 22 or German Application 19 548 289.1, simultaneously or in succession, for example in a distillation column or in a sidestream takeoff column having a dividing wall (Petlyuk column), so that the condensation temperature of the downstream purification column in the AMCPA removal is generally higher and condensation is facilitated. The low boiling DACH, if present, can with advantage be separated off together with AMCPA, but the removal of DACH can also be effected overhead in a separate column.

It is advantageous to precede the purification of the hexamethylenediamine by the process of this invention by complete or partial removal of low boilers, such as HMI, if present.

In the mixture comprising hexamethylenediamine and AMCPA, THE pre-separation weight proportion of AMCPA, based on hexamethylenediamine, is generally within the range from 1 to 10,000 ppm, especially 10 to 10,000, more especially within the range from 100 to 1000 ppm, although the process of the invention is not restricted to these limits.

The separation of AMCPA from the mixture is carried out according to the invention by distillation at pressures from 1 to 300 mbar, preferably from 1 to 200 mbar, which results in bottom temperatures within the range from 40 to 160° C.

The post-separation weight proportion of 2-aminomethylcyclopentylamine, based on the recovered hexamethylenediamine product, is within the range from 0 to 100 ppm.

The distillation can be carried out in customary apparatus as described for example in: Kirk-Othmer, Encyclopedia of Chemical Technology, 3rd Ed., Vol. 7, John Wiley & Sons, New York, 1979, pages 870–881, such as sieve plate columns, bubble cap columns or packed columns.

Preference is given to a distillation apparatus having a pressure drop from bottom to top within the range from 0 to 200 mbar, preferably within the range from 0 to 50 mbar, and the pressure should advantageously be within the range from 3 to 300 mbar, especially within the range from 3 to 200 mbar, at the bottom and within the range from 1 to 300 mbar, especially within the range from 1 to 200 mbar, at the top.

It is particularly advantageous to use distillation columns having a low pressure drop, preferably not more than 1 mbar, especially 0.5 mbar, per theoretical plate.

The use of any conventional distillation apparatus is contemplated such as distillation columns or vessels known in the chemical arts.

Columns which are especially suitable are packed columns, preferably with arranged packing such as metal sheet packing, especially woven wire packing.

The process of the invention affords the AMCPA as overhead product, in general, if present in the mixture comprising essentially hexamethylenediamine and AMCPA, in the mixture with DACH and low boiling components.

The distillation can be carried out in a plurality of columns, such as 2 or 3 columns, but is advantageously carried out in a single column.

Hexamethylenediamine can be processed with dicarboxylic acids such as adipic acid into industrially important polymers.

EXAMPLES

Invention Example 1

10 kg/h of HMD having an AMCPA content of 300 ppm were fed into a column having a low pressure drop woven packing corresponding to 100 theoretical plates. The top of the column was adjusted to a pressure of 100 mbar, and the pressure at the bottom was measured as 140 mbar. At the top of the column, a constant 6 g/h of product were removed and 50 kg/h recycled into the column as reflux.

The AMCPA content of the hexamethylenediamine obtained as bottom product was below the detection limit of 1 ppm, while the hexamethylenediamine content of the overhead product was 50.2% by weight.

Invention Example 2

Invention Example 1 was repeated, except that the top of the column was adjusted to a pressure of 250 mbar and a pressure of 305 mbar was measured at the bottom.

The AMCPA content of the hexamethylenediamine obtained as bottom product was 11 ppm, while the hexamethylenediamine content of the overhead product was 51.9% by weight.

Comparative Example 1

Invention Example 1 was repeated, except that the top of the column was adjusted to a pressure of 500 mbar and a pressure of 545 mbar was measured at the bottom.

The AMCPA content of the hexamethylenediamine obtained as bottom product was 48 ppm, while the hexamethylenediamine content of the overhead product was 58.2% by weight.

Comparative Example 2

10 kg/h of HMD having an AMCPA content of 300 ppm were fed into a sieve plate column having 140 sieve plates. The top of the column was adjusted to a pressure of 100 mbar, and the pressure at the bottom was measured as 900 mbar. At the top of the column, a constant 6 g/h of product were removed and 50 kg/h recycled into the column as reflux.

The AMCPA content of the hexamethylenediamine obtained as bottom product was 22 ppm, while the hexamethylenediamine content of the overhead product was 53.7% by weight.

We claim:

1. A process for separating 2-aminomethylcyclopentylamine from a mixture consisting of hexamethylenediamine and 2-aminomethylcyclopentylamine, which comprises performing the separation in a distillation apparatus by distilling at a pressure from 1 to 300 mbar and recovering the hexamethylenediamine as bottom product.

2. A process as claimed in claim 1, wherein the pressure drop between the top and the bottom of the distillation apparatus is within the range from 0 to 200 mbar.

3. A process as claimed in claim 1, wherein the pressure at the bottom of the distillation apparatus is within the range from 3 to 300 mbar.

4. A process as claimed in claim 1, wherein the pressure at the top of the distillation apparatus is within the range from 1 to 300 mbar.

5. A process as claimed in claim 1, wherein the distillation apparatus used is a distillation column.

6. A process as claimed in claim 1, wherein the distillation apparatus used is a packed column.

7. A process as claimed in claim 1, wherein the distillation apparatus used is a distillation column having a pressure drop of not more than 1 mbar per theoretical plate.

8. A process as claimed in claim 1, wherein the weight proportion of 2-aminomethylcyclopentylamine, based on hexamethylenediamine prior to separation, is within the range from 1 to 10,000 ppm.

9. A process as claimed in claim 1, wherein the weight proportion of 2-aminomethylcyclopentylamine, based on hexamethylenediamine after separation, is within the range from 0 to 100 ppm.

* * * * *